United States Patent [19]

Mizuno et al.

[11] Patent Number: 4,892,973

[45] Date of Patent: Jan. 9, 1990

[54] PROCESS FOR PRODUCING 1,1-DIPHENYLALKENES

[75] Inventors: Kozo Mizuno, Uji; Hideaki Fujisaki, Kyoto; Yoshinori Uda, Kyoto; Tadashi Imai, Kyoto; Katsuhiko Tsunemitsu, Kyoto, all of Japan

[73] Assignee: Yamada Chemical Co., Ltd., Kyoto, Japan

[21] Appl. No.: 239,072

[22] Filed: Aug. 31, 1988

Related U.S. Application Data

[63] Continuation of Ser. No. 785,500, Oct. 8, 1985, abandoned.

[30] Foreign Application Priority Data

Oct. 12, 1984 [JP] Japan ................................. 59-214982

[51] Int. Cl.$^4$ .................... C07C 87/14; C07D 209/00; C07D 207/00

[52] U.S. Cl. .................................... 564/315; 548/524; 548/454; 546/99; 546/135; 540/596

[58] Field of Search ................ 548/524, 454; 564/315; 546/99, 135; 540/596

[56] References Cited

PUBLICATIONS

Gilbert et al., Chem. Abstracts, vol. 99 (1983), entry 68719.

*Primary Examiner*—Mukund J. Shah
*Assistant Examiner*—Frederick F. Tsung
*Attorney, Agent, or Firm*—John P. White

[57] ABSTRACT

Disclosed herein is a novel process for producing 1,1-diphenylalkenes, comprising contacting lead peroxide with 1,1-diphenylalkanes having the structure wherein a nitrogen atom of a tertiary amino group is bonded to the para-position of each of the two benzene rings of the 1,1-diphenylalkane, thereby obtaining the corresponding 1,1-diphenylalkenes.

5 Claims, No Drawings

1

PROCESS FOR PRODUCING 1,1-DIPHENYLALKENES

This is a continuation of application Ser. No. 785,500, filed Oct. 8, 1985 now abandoned.

BACKGROUND OF THE INVENTION

The present invention relates to a novel process for producing 1,1-diphenylalkenes, and more in detail the present invention relates to a process for producing 1,1-diphenylalkenes comprising contacting lead peroxide with the corresponding 1,1-diphenylalkanes, thereby obtaining directly 1,1-diphenylalkenes without passing through the state of a 1,1-diphenylketone.

Although the 1,1-diphenylalkenes as the object compounds of the present invention are important as dyestuffs and as the starting materials for the dyestuffs of the more complicated structure, it has been necessary hitherto for obtaining 1,1-diphenylalkenes to synthesize 1,1-diphenylalkenes via a 1,1-diphenylketone by a Grignard reaction or by a Wittig reaction. In either case, it has been inevitable to adopt a process in which the presence of water or moisture is extremely detrimental and accordingly, it has been difficult to industrially form the 1,1-diphenylalkenes, and a more inexpensive industrial process for producing the 1,1-diphenylalkenes has been keenly demanded.

The present invention offers an inexpensive process for producing the 1,1-diphenylalkenes complying with the above-mentioned object.

SUMMARY OF THE INVENTION

In an aspect of the present invention, there is provided a process for producing a 1,1-diphenylalkene, comprising contacting lead peroxide with a 1,1-diphenylalkane having the structure wherein the nitrogen atom of a tertiary amino group has been bonded to the para-position of each of the two benzene rings of said 1,1-diphenylalkane, thereby obtaining the corresponding 1,1-diphenylalkene.

DETAILED EXPLANATION OF THE INVENTION

The characteristic of the process according to the present invention is in that a 1,1-diphenylalkane having the structure in which a nitrogen atom of a tertiary amino group is bonded to the para-position of each of the two benzene rings of the 1,1-diphenylalkane is contacted with lead peroxide, thereby obtaining the corresponding 1,1-diphenylalkene.

The 1,1-diphenylalkane having the structure in which a nitrogen atom of a tertiary amino group is bonded to the para-position of each of the two benzene rings of the 1,1-diphenylalkane is the compound represented by the formula (1):

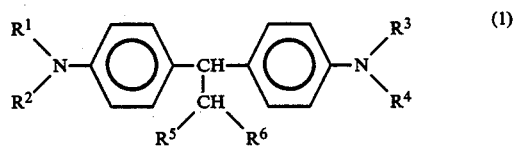

wherein $R^1$, $R^2$, $R^3$ and $R^4$ represent independently a $(C_1-C_6)$ alkyl group, a cyclo $(C_3-C_{12})$ alkyl group, an aryl $(C_1-C_6)$ alkyl group or an alkylene group forming a heterocyclic ring by bonding to the carbon atom at the ortho-position of the benzene ring to which the nitrogen atom is bonded or $R^1$ and $R^2$, and $R^3$ and $R^4$ respectively, may form the respective heterocyclic rings together with the nitrogen atom, $R^5$ and $R^6$ represent independently a hydrogen atom, a $(C_1-C_{10})$ alkyl group, a cyclo $(C_3-C_{12})$ alkyl group, an aryl group which may have substituent(s) or an aryl $(C_1-C_6)$ alkyl group which may have substituent(s), or $R^5$ and $R^6$ may form a ring by mutual coupling.

As the compounds most simply represented by the formula (1), for instance, 1,1-bis(4-dimethylaminophenyl)ethane, 1,1-bis(4-dimethylaminophenyl)propane, 1,1-bis(4-dimethylaminophenyl)butane, 1,1-bis(4-dimethylaminophenyl)isobutane, bis(4-dimethylaminophenyl)methylcyclohexane and the like may be exemplified. In the case where the dimethylamino group of the compound is substituted by a diethylamino group, a pyrrolidino group, a piperidino group, a hexamethyleneimino group or the like optionally, the compounds represented by the formula (1), provided with a more complicated structure are obtained. Further, it is possible that the compounds of a more complicated structure are available by selecting $R^1$ to $R^6$ of the formula (1).

Each of the above-mentioned 1,1-diphenylalkanes can be easily synthesized by reacting an aldehyde,

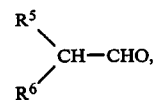

with two aminobenzenes,

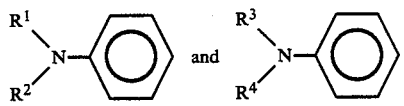

as has been known:

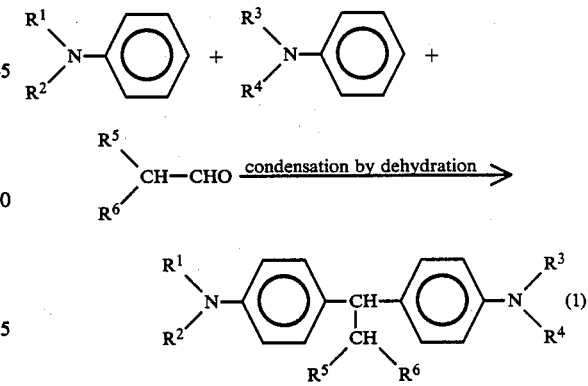

It can be relatively easy for the persons skilled in the art to forecast that in the case where an oxidant acts on a 1,1-diphenylalkane represented by the formula (1), the 1,1-diphenylalkane is converted to a compound of 1,1-diphenylcarbinol represented by the formula (2) and then, a dehydration occurs between the hydroxy group of the carbinol and the hydrogen atom bonding to the adjacent carbon atom thereof to form the 1,1-diphenylalkene represented by the formula (3), however, it has been found by the present inventors that the above-mentioned process is very difficult to be actually realized.

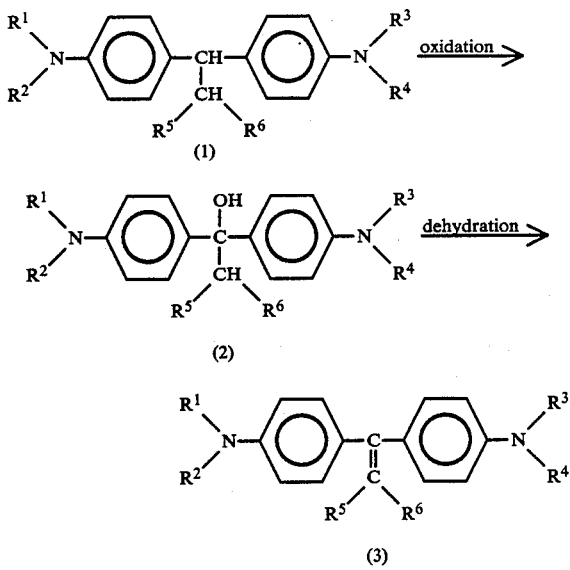

Namely, it has been found by the present inventors that in spite of the present inventors' broad research, all the oxidants generally used for oxidation such as salts of bichromic acid, permanganic acid and persulfuric acid, chromic acid, manganese dioxide, hydrogen peroxide and gaseous oxygen in the presence of a catalyst are unsuitable for the above-mentioned oxidation because of the formation of the oxidation product other than the object product or not causing any oxidation, and that only the oxidant which gives the object product is lead peroxide.

Accordingly, the use of lead peroxide as the oxidant is indispensable in the process according to the present invention.

Any method may be adopted for obtaining the 1,1-diphenylalkene represented by the formula (3) by contacting the 1,1-diphenylalkane represented by the formula (1) with lead peroxide, however, it is preferable for carrying out the industrially profitable process to contact the 1,1-diphenylalkane dissolved in an aqueous solvent with lead peroxide. Since the 1,1-diphenylalkane represented by the formula (1) has amino groups, there are many cases where the diphenylalkane is soluble in acidic water. In the case where the solubility thereof in the solvent is insufficient, it is desirable to use methanol, ethanol, glycols, dimethylformamide, acetic acid and the like together with water for solubilizing the diphenylalkane and to submit the solubilized diphenylalkane to the reaction.

When the diphenylalkane represented by the formula (1) is contacted in the solubilized state with lead peroxide, the diphenylalkane is instantaneously oxidized and converted into the diphenylalkene represented by the formula (3). Although there may be cases where a 1,1-diphenylcarbinol represented by the formula (2) is formed as the intermediate product according to the species of the substituent thereof, the diphenylcarbinol is hardly present in a stable state, and is easily dehydrated and converted to the diphenylalkene represented by the formula (3) by thermal treatment or treatment with an acid or an alkali.

Since the reaction rate of formation of 1,1-diphenylalkene according to the process of the present invention is large and the generation of heat in the reaction is conspicuous, it is desirable for obtaining the reaction product in a favorable yield to use a large amount of the solvent and also to carry out the reaction at a temperature as low as possible, for example $-30°$ to $30°$ C., preferably $-20°$ to $20°$ C. Lead peroxide of fine-grained particles generally used is suitable, and it is used in an amount larger than the theoretical amount to the amount of diphenylalkane, preferably 1 to 3 mol % based on 1 mol % of the diphenylalkane.

Since the diphenylalkene is formed in a state of a solution or a slurry as the result of reaction in the reaction system, it is separated from the other materials, i.e., the unreacted starting materials and the by-products, by the combination of operations suitable for the state of the diphenylalkene such as neutralization, filtration, extraction, etc., and thus it can be purified and then collected.

Because of the use of lead peroxide in the process according to the present invention, it is favorable to carry out the reaction in an aqueous acidic solution (pH 1–7), and it is preferable to use hydrochloric acid or nitric acid as the acid in the range of 2 to 20 mol % based on 1 mol % of the diphenylalkane. Namely, in the case of using hydrochloric acid or nitric acid, the amount of lead peroxide which is little in excess of the theoretical amount is sufficient, however, in the case of using the other species of acids, there are cases wherein a relatively large excess amount of lead peroxide is necessary, and in such cases, the isolation of the object product from the reaction mixture is generally not easy.

The present invention will be explained more in detail while referring to the following non-limitative examples. Although in the examples, only the diphenylalkanes represented by the formula (1) wherein $R^1$ is the same as $R^3$ and also $R^2$ is the same as $R^4$, namely those having the symmetrical structure are shown, it goes without saying that the present invention does not exclude those having the unsymmetrical structure.

EXAMPLE 1

1-1: Production of 1,1-bis(4-dimethylaminophenyl)ethane

In a reaction vessel, 2 mols (242 g) of dimethylaniline, 400 ml of water, 348 g of aqueous 62% solution of sulfuric acid and 1 g of p-toluenesulfonic acid were introduced, and after adding 110 g of paraldehyde into the reaction vessel, the mixture was kept at 55° C. for 7 days under stirring. After neutralizing the reaction mixture with sodium hydroxide, the thus formed oily matter was separated from the aqueous layer, and by blowing steam into the oily matter, the unreacted dimethylaniline was removed therefrom. By introducing the residual tarry matter into methanol and washing it with methanol, 150 g of 1,1-bis(4-dimethylaminophenyl)ethane of a melting point of 68° C. were obtained.

1-2: Synthesis of 1,1-bis(4-dimethylaminophenyl)ethylene 0.1 mol (26.8 g) of the thus obtained 1,1-bis(4-dimethylaminophenyl)ethane was dissolved in 200 ml of water containing 0.4 mole of nitric acid, and by adding 300 g of ice to the solution, the temperature of the solution was made to 0° C. The thus cooled solution was introduced into a dispersion of 0.13 mole of lead peroxide of a fine-grained state in 4 liters of water added with 2.5 kg of ice while stirring the dispersion well. The reaction mixture showed a coloration to blue instantly. A solution of 28 g of sodium sulfate in 100 ml of water was added to the reaction mixture to precipitate lead sulfate, and then the liquid reaction mixture was neutralized with an aqueous solution of sodium hydroxide. Since the organic compound precipitated as crystals, the whole matter was filtered to collect the precipitate and the thus collected precipitate was dried.

By extracting the organic compound with use of toluene from the thus dried precipitate, and condensing the liquid extract, the oxidation product was obtained as a solid matter.

In the case where the solid matter was developed by a thin layer chromatography of silica gel, the spot of the major product (blue in colour) coincided with the spot of 1,1-bis(4-dimethylaminophenyl)ethylene obtained by the Grignard reaction of methyl magnesium iodide and Michler's ketone.

Although there were formed some spots of the by-products, one of them showed the same Rf value as that of 1,1-bis(4-dimethylaminophenyl)ethylene when re-developed after developing on the thin layer of silica gel and drying, and accordingly, the one spot of them was believed to be due to 1,1-bis(4-dimethylaminophenyl)ethanol.

Pure 1,1-bis(4-dimethylaminophenyl)ethylene can be obtained by recrystallizing the oxidation product from ethanol in a yield of 9 g. It melts at 115° C.

EXAMPLE 2

Syntheses of other 1,1-diphenylethanes and -ethylenes

In the same manner as in 1-1 of Example 1 except for using each of aminobenzenes shown in Table 1 instead of dimethylaniline in Example 1 (1-1), each of the corresponding diphenylethanes was produced, and in the same manner as in 1-2 of Example 1 except for using each of the thus obtained diphenylethanes instead of 1,1-bis(4-dimethylaminophenyl)ethane in 1-2 of Example 1 (namely, oxidizing thereof by lead peroxide), each of the corresponding diphenylethylenes was obtained. The fact of formation of the diphenylethylenes was confirmed by the blue spot developed on a thin layer chromatogram of silica gel (the spot showing the absorption peak in a range of from 600 to 615 nm according to refraction spectrographic determination). 1,1-Diphenylethanes before subjecting to oxidation are almost colourless on the thin layer chromatogram of silica gel and they showed a fluorescence by ultraviolet light. Accordingly, the success or failure in oxidation can be easily discriminated.

TABLE 1

| Aminobenzene | Diphenylethane | Diphenylethylene |
|---|---|---|

TABLE 1-continued

| Aminobenzene | Diphenylethane | Diphenylethylene |
|---|---|---|

EXAMPLE 3

In the same manner as in 1-1 of Example 1 except for using N-phenylpyrrolidine instead of dimethylaniline in 1-1 of Example 1, the condensation was completed after about 12 hours and 1,1-bis(4-pyrrolidinylphenyl)ethane (m.p. 112° C.) was obtained in a yield of higher than 90%.

In the same manner as in 1-2 of Example 1 except for using the thus obtained 1,1-bis(4-pyrrolidinylphenyl)ethane instead of 1,1-bis(4-dimethylaminophenyl)ethane and using hydrochloric acid instead of nitric acid in 1-2 of Example 1, 1,1-bis(4-pyrrolidinylphenyl)ethylene (m.p. 211° C.) was obtained in a yield of about 50%.

In the above-mentioned reaction, the formation of 1,1-bis(4-pyrrolidinylphenyl)ethanol was not recognized at all.

EXAMPLE 4

In the same manner as in 1-1 of Example 1 except for using N-phenylpyrrolidine instead of dimethylaniline and using each of the aldehydes shown in Table 2 instead of paraldehyde in 1-1 of Example 1, each of the corresponding 1,1-diphenylalkanes shown in Table 2 was obtained.

By the oxidation by lead peroxide in the same manner as in 1-2 of Example 1 except for using hydrochloric acid instead of nitric acid and using each of the thus produced 1,1-diphenylalkanes instead of 1,1-bis(4-dimethylaminophenyl)ethane in 1-2 of Example 1, each of the corresponding diphenylalkenes shown in the right column of Table 2 was obtained. The fact was recognized by the blue spot on the thin layer silica gel chromatogram.

As are seen above, the present invention offers an industrially profitable process for producing 1,1-diphenylalkenes without passing through the conventional reaction steps which are disturbed by the presence of moisture.

TABLE 2

| Aminobenzene | Aldehyde | Diphenylalkane | Diphenylalkene |
|---|---|---|---|
| (pyrrolidinyl-phenyl) | CH₃CH₂CH₂CHO | pyrrolidinyl-C₆H₄–CH(CH₂CH₂CH₃)– | pyrrolidinyl-C₆H₄–C(=CH–C₂H₅)– |
| " | CH₃(CH₂)₆CHO | pyrrolidinyl-C₆H₄–CH(CH₂)₆CH₃– | pyrrolidinyl-C₆H₄–C(=CH–C₆H₁₃)– |
| " | (CH₃)₂CH–CHO | pyrrolidinyl-C₆H₄–CH–CH(CH₃)₂ | pyrrolidinyl-C₆H₄–C=C(CH₃)₂ |
| " | cyclohexyl-CHO | pyrrolidinyl-C₆H₄–CH–(cyclohexyl) H | pyrrolidinyl-C₆H₄–C=(cyclohexylidene) H |
| " | C₆H₅–CH₂CHO | pyrrolidinyl-C₆H₄–CH–CH₂–C₆H₅ | pyrrolidinyl-C₆H₄–C=CH₂ (with C₆H₅) |
| " | C₆H₅–CH₂CH₂CHO | pyrrolidinyl-C₆H₄–CH–CH₂CH₂–C₆H₅ | pyrrolidinyl-C₆H₄–C=CH–CH₂–C₆H₅ |
| " | C₆H₅–CH(CH₃)–CHO | pyrrolidinyl-C₆H₄–CH–CH(CH₃)(C₆H₅) | pyrrolidinyl-C₆H₄–C=C(CH₃)(C₆H₅) |
| " | OHC–CHO | (pyrrolidinyl-C₆H₄–CH–)₂ | (pyrrolidinyl-C₆H₄–C=)₂ |

TABLE 2-continued

| Aminobenzene | Aldehyde | Diphenylalkane | Diphenylalkene |
|---|---|---|---|
| " | OHC—CH$_2$—CHO | (N-C$_6$H$_4$-)$_2$CH—CH$_2$CH(-C$_6$H$_4$-N)$_2$ | (N-C$_6$H$_4$-)$_2$C=CH—CH(-C$_6$H$_4$-N)$_2$ |
| " | OHC—(CH$_2$)$_3$—CHO | (N-C$_6$H$_4$-)$_2$CH—(CH$_2$)$_3$CH(-C$_6$H$_4$-N)$_2$ | (N-C$_6$H$_4$-)$_2$C=CH—CH$_2$—CH=C(-C$_6$H$_4$-N)$_2$ |

What is claimed is:

1. A process for producing a 1,1-diphenylalkene represented by the formula:

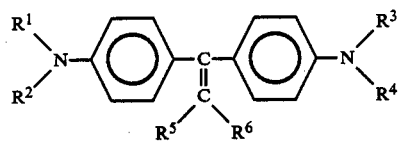

which comprises dissolving a 1,1-diphenylalkane in an aqueous solvent by adding thereto 2 to 20 mol of an acid based on 1 mol of the 1,1-diphenylalkane and contacting lead peroxide with the 1,1-diphenylalkane in the thus obtained aqueous acidic solution at a temperature of −30° to 30° C., wherein the molar ratio of the lead peroxide to the 1,1-diphenylalkane is 1 to 3:

the 1,1-diphenylalkane being represented by the formula:

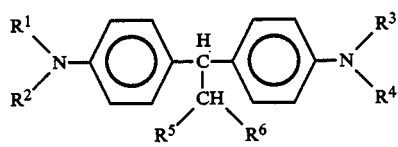

wherein $R^1$, $R^2$, $R^3$ and $R^4$ each independently represent an ($C_1$–$C_6$) alkyl group, a ($C_3$–$C_{12}$) cycloalkyl group, an aryl ($C_1$–$C_6$) alkyl group, or an alkylene group which forms a heterocyclic ring comprising the nitrogen atom to which it is bound and the carbon atom at the ortho-position of the benzene ring bound to the nitrogen atom, or $R^1$ and $R^2$ are bound to one another and form a heterocyclic ring comprising the nitrogen atom to which they are bound, or $R^3$ and $R^4$ are bound to one another and form a heterocyclic ring comprising the nitrogen atom to which they are bound; and wherein $R^5$ and $R^6$ each independently represent a hydrogen atom, an ($C_1$–$C_{10}$) alkyl group, a ($C_3$–$C_{12}$) cycloalkyl group, or an aryl or substituted aryl ($C_1$–$C_6$) alkyl group.

2. A process according to claim 1, wherein the contacting is carried out at a temperature of −20° to 20° C.

3. A process according to claim 1 or 2, wherein the acid added to the aqueous solvent is hydrochloric acid, nitric acid or acetic acid.

4. A process according to claim 1 or 2, wherein a solvent selected from the group consisting of methanol, ethanol, glycols and dimethylformamide is added to the aqueous solvent for solubilizing the 1,1-diphenylalkane.

5. A process according to claim 1, 2, 3 or 4, wherein said $R^1$, $R^2$, $R^3$ and $R^4$ each independently represent an ($C_1$–$C_6$) alkyl group, a cyclohexyl group, a phenylmethyl group, or an alkylene group which forms a heterocyclic ring comprising the nitrogen atom to which it is bound and the carbon atom at the ortho-position of the benzene ring bound to the nitrogen atom, the heterocyclic ring being selected from

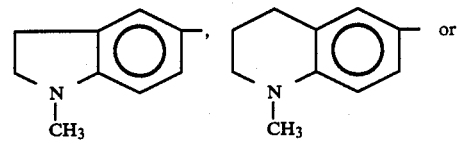

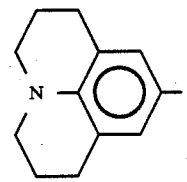

or said $R^1$ and $R^2$ are bound to one another and form a heterocyclic ring comprising the nitrogen atom to which they are bound, the heterocyclic ring being selected from

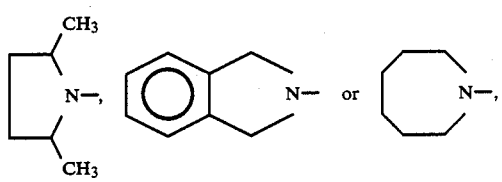

or said $R^3$ and $R^4$ are bound to one another and form a heterocyclic ring comprising the nitrogen atom to which they are bound, the heterocyclic ring being selected from

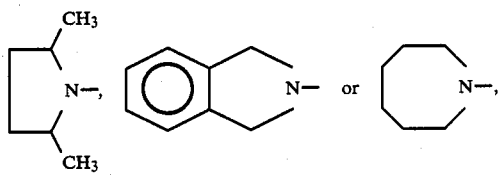

and wherein said $R^5$ and $R^6$ each represent a hydrogen atom.

* * * * *